United States Patent [19]

Prencipe et al.

[11] Patent Number: 5,424,059
[45] Date of Patent: * Jun. 13, 1995

[54] ANTIBACTERIAL ANTIPLAQUE DENTIFRICE

[75] Inventors: Michael Prencipe, East Windsor; Anthony R. Volpe, Somerset; Kedar N. Rustogi, Kendall Park; Vincent O. Drago, Highland Park; Abdul Gaffar, Princeton, all of N.J.

[73] Assignee: Colgate Palmolive Company, New York, N.Y.

[*] Notice: The portion of the term of this patent subsequent to Jan. 16, 2007 has been disclaimed.

[21] Appl. No.: 160,337

[22] Filed: Dec. 1, 1993

Related U.S. Application Data

[60] Continuation-in-part of Ser. No. 984,629, Dec. 12, 1992, Pat. No. 5,312,618, which is a division of Ser. No. 758,345, Sep. 9, 1991, Pat. No. 5,192,531, which is a continuation of Ser. No. 399,669, Aug. 25, 1989, abandoned, which is a continuation-in-part of Ser. No. 291,712, Dec. 29, 1988, Pat. No. 4,894,220, and a continuation-in-part of Ser. No. 346,258, May 1, 1989, Pat. No. 5,043,154, which is a continuation of Ser. No. 8,901, Jan. 30, 1989, abandoned, said Ser. No. 291,712, is a continuation-in-part of Ser. No. 8,901, Jan. 30, 1989, abandoned.

[51] Int. Cl.⁶ .......................... A61K 7/16; A61K 7/18
[52] U.S. Cl. ................................ 424/52; 424/49
[58] Field of Search ....................... 424/49-58

[56] References Cited

U.S. PATENT DOCUMENTS

| | | | |
|---|---|---|---|
| 3,932,604 | 1/1976 | Barth | 424/49 |
| 3,970,747 | 7/1976 | Barth | 424/52 |
| 4,291,017 | 9/1981 | Beierle et al. | 424/52 |
| 4,894,220 | 1/1990 | Nabi et al. | 424/52 |
| 4,927,625 | 5/1990 | Duckworth | 424/52 |
| 4,935,227 | 6/1990 | Duckworth | 424/52 |
| 4,945,087 | 7/1990 | Talwar et al. | 514/60 |
| 4,950,479 | 8/1990 | Hill et al. | 424/49 |
| 5,032,386 | 7/1991 | Gaffar et al. | 424/49 |
| 5,032,387 | 7/1991 | Hill et al. | 424/49 |
| 5,037,635 | 8/1991 | Nabi et al. | 424/52 |
| 5,037,637 | 8/1991 | Gaffar et al. | 424/52 |
| 5,043,154 | 8/1991 | Gaffar et al. | 424/52 |
| 5,080,887 | 1/1992 | Gaffar et al. | 424/52 |
| 5,089,255 | 2/1992 | Gaffar et al. | 424/52 |
| 5,144,024 | 9/1992 | Pepper et al. | 536/128 |
| 5,156,835 | 10/1992 | Nabi et al. | 424/52 |
| 5,178,869 | 1/1993 | Ebine et al. | 424/401 |
| 5,192,531 | 3/1993 | Gaffar et al. | 424/52 |
| 5,292,526 | 3/1994 | Gaffar et al. | 424/49 |
| 5,296,214 | 3/1994 | Gaffar | 424/49 |
| 5,316,758 | 5/1994 | Morishima et al. | 424/54 |

OTHER PUBLICATIONS

Rolla et al E.P. 251146 (Jan. 7, 1988) C.A. 108:81860, Derwent Abstract.
Goupil E.P. 138705 (Apr. 24, 1985).
Simone et al Medline Abstract J. Dent. Res. 71 Spec. No. 864–6 Apr. 1992.
Duckworth III Medline Abstract Int. Dent. J. 43(6 Suppl. 1) 529–539 Dec. 1993.
Firestone et al J. Dent. Res. 65(1):44–48 (1986) C.A. 104:105436.

*Primary Examiner*—Shep K. Rose
*Attorney, Agent, or Firm*—Robert L. Stone; Robert C. Sullivan; Murray M. Grill

[57] ABSTRACT

A dentifrice which inhibits plaque formation and reduces gingivitis and caries comprising water-insoluble alkaline earth metal polishing agent such as dicalcium or dimagnesium phosphate or pyrophosphate, xylitol and a substantially water insoluble noncationic antibacterial agent, such as triclosan.

15 Claims, No Drawings

ANTIBACTERIAL ANTIPLAQUE DENTIFRICE

This application is a continuation-in-part of Ser. No. 07/984,629, filed Dec. 12, 1992;, now U.S. Pat. No. 5,312,618 which is a Division of Ser. No. 758,345, filed Sep. 9, 1991, now U.S. Pat. No. 5,192,531, issued Mar. 9, 1993, which is a continuation of Ser. No. 07/399,669, filed Aug. 25, 1989, now abandoned, which is a continuation-in-part of each of Ser. No. 07/291,712, filed Dec. 29, 1988, now U.S. Pat. No. 4,894,220, issued Jan. 16, 1990, and of Ser. No. 07/346,258, filed May 1, 1989, now U.S. Pat. No. 5,043,154, issued Aug. 27, 1991, which Ser. No. 07/291,712 and Ser. No. 07/346,258 are respectively a continuation-in-part and a continuation of Ser. No. 07/008,901, filed Jan. 30, 1989, now abandoned.

This invention relates to an antibacterial antiplaque dentifrice. More particularly, it relates to a dentifrice containing a substantially water-insoluble noncationic antibacterial agent effective to inhibit plaque.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurrence of gingivitis and caries.

Indeed, with regard to caries occurrence, it is believed that ways anticaries effects of dentifrices are increased by: 1) Increasing degree of saturation (DS) with respect to enamel by increasing the activities of F, Ca, and P in plaque and plaque fluid; and 2) Increasing the pH buffering capacity of plaque (Margolis, H. C., Duckworth, J. H., Moreno, E. C. J Dent res, 67(12), (1982) 1476-1482). A further increase in anticaries effects of dentifrices is achieved with use of an antibacterial agent reducing the amount of acid producing bacteria in plaque.

Accordingly, it is highly desirable to include antimicrobial agents which have been known to reduce plaque in oral compositions. Frequently, cationic antibacterial agents have been suggested. Moreover, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic material such as guanides and quaternary ammonium compounds as well as non-cationic compounds such as halogenated salicylanilides and halogenated hydroxydiphenyl ethers. The noncationic antibacterial antiplaque halogenated hydroxydiphenyl ether, triclosan, has also been described in combination with zinc citrate trihydrate in European Patent Publication 0161,899 to Saxton et al. Triclosan is also disclosed in European Patent Publication 0271,332 to Davis as a toothpaste component in a carrier system containing a solubilizing agent such as propylene glycol.

The cationic antibacterial materials such as chlorhexidine, benzethonium chloride and cetyl pyridinium chloride have been the subject of greatest investigation as antibacterial antiplaque agents. However, they are generally not effective when used with anionic materials. Noncationic antibacterial materials such as triclosan on the other hand, can be compatible with anionic components in an oral composition.

However, oral compositions typically are mixtures of numerous components and even such typically neutral materials as humectants can affect performance of such components.

Moreover, even noncationic antibacterial antiplaque agents may have limited antiplaque effectiveness with commonly used materials such as polyphosphate anticalculus agents which are disclosed together in British Patent Publication 22 00551 of Gaffar et al and in EP 0251591 of Jackson et al. In commonly assigned U.S. Pat. No. 5,180,578 it is shown that the antiplaque effectiveness is greatly enhanced by including an antibacterial-enhancing agent (AEA) which enhances the delivery of said antibacterial agent to, and retention thereof on, oral surfaces, and by providing optimized amounts and ratios of polyphosphate and AEA.

Further, even when polyphosphate anticalculus agent is not present as in commonly assigned U.S. Pat. No. 5,192,530, antiplaque effectiveness on soft oral tissue is optimized by including the AEA and a solubilizing material which dissolves the noncationic antibacterial agent in saliva when the polishing agent is a siliceous polishing agent present in amount of about 5-30%. Indeed, when the amount of noncationic antibacterial agent is optimized, even the special solubilizing material is not required, as in commonly assigned U.S. Pat. No. 5,156,835.

It has been reported that plaque grown in the presence of xylitol is less acidic than plaque grown under control conditions. (Makinen, K.K. "Latest Dental Studies On Xylitol And Mechanism Of Action Of Xylitol In Caries Limitation", Grenby, T. H., Ed; *Elsevier Applied Science,* pp. 331-362 (1990).

There are a number of patent disclosures which describe the optional presence of xylitol as a sweetener ingredient or a humectant in oral compositions which contain or may contain a noncationic antibacterial agent such as triclosan. These include ancestor U.S. Pat. Nos. 5,192,531; 5,043,154 and 4,894,220 as well as companion patents U.S. Pat. Nos. 5,192,530; 5,188,821; 5,180,578; 5,178,851; 5,156,835; 5,080,887; 5,037,637; 5,037,635 and 5,032,286. Similar optional disclosures occur in U.S. Pat. Nos. 5,202,111; 5,192,533; 5,096,700; 4,935,227 and 4,927,625, as well as in Lion Dentifrice Company-Japanese Patent Disclosures H2-11511; H3-5410; H4-13918; and H4-13919. The art did not recognize that noncationic antibacterial agent in combination with xylitol could provide a substantially improved effect on microbial metabolism and further reduce the acidogenic characteristics of plaque.

Furthermore, the prior art did not recognize that plaque reduction with noncationic antibacterial agent and xylitol could be additionally improved by including dentally acceptable water-insoluble alkaline earth metal polishing agents in the oral composition. Such insoluble alkaline earth metal salts can provide alkaline earth metal such as calcium or magnesium which can then be incorporated in plaque and is released under acidogenic conditions to increase the degree of saturation with respect to enamel and prevent dissolution of teeth leading to a lower caries incidence. Such insoluble calcium salts act as buffers against acid produced by plaque, and are also effective abrasives to remove plaque and food debris.

It is an advantage of this invention that an oral composition is provided which is highly effective against plaque growth.

It is a further advantage of this invention that an antiplaque oral composition is provided which is effective to reduce the occurrence of caries and gingivitis.

Additional advantages of this invention will be apparent from consideration of the following specification.

In accordance with certain of its aspects, this invention relates to an antibacterial antiplaque dentifrice comprising in an orally acceptable aqueous humectant vehicle, about 20–75% of a dentally acceptable water-insoluble alkaline earth metal salt polishing agent, an effective antiplaque active ingredient amount of a substantially water insoluble noncationic antibacterial agent and at least about 0.1% by weight of xylitol.

Typical examples of water insoluble noncationic antibacterial agents which are particularly desirable from considerations of antiplaque effectiveness, safety and formulation are:

HALOGENATED DIPHENYL ETHERS

2',4,4'-trichloro-2-hydroxy-diphenyl ether (Triclosan)
2,2'-dihydroxy-5,5'-dibromo-diphenyl ether

Halogenated Salicylanilides

4',5-dibromosalicylanilide
3,4',5-trichlorosalcylanilide
3,4',5-tribromosalicylanilide
2,3,3',5-tetrachlorosalicylanilide
3,3,3', 5-tetrachlorosalicylanilide
3,5-dibromo-3'-trifluoromethylsalicylanilide
5-n-octanoyl-3'-trifluoromethylsalicylanilide
3,5-dibromo-4'-trifluoromethylsalicylanilide
3,5-dibromo-3'-trifluoromethylsalicylanilide (Fluorophene)

| Benzoic Esters | |
|---|---|
| Methyl | -p-Hydroxybenzoic Ester |
| Ethyl | -p-Hydroxybenzoic Ester |
| Propyl | -p-Hydroxybenzoic Ester |
| Butyl | -p-Hydroxybenzoic Ester |

SESQUITERPENE ALCOHOLS

Farnesol
Nerolidol
Bisabolol
Santalol

HALOGENATED CARBANILIDES 3,4,4'-trichlorocarbanilide
3-trifluoromethyl-4,4'-dichlorocarbanilide
3,3,4'-trichlorocarbanilide Phenolic Compounds (including phenol and its homologs, mono- and polyalkyl and aromatic halo (e.g. F, Cl, Br, I)-phenols, resorcinol and catechol and their derivatives and bisphenolic compounds). Such compounds include inter alia:

| Phenol and its Homologs | |
|---|---|
| Phenol | |
| 2 Methyl | -Phenol |
| 3 Methyl | -Phenol |
| 4 Methyl | -Phenol |
| 4 Ethyl | -Phenol |
| 2,4-Dimethyl | -Phenol |
| 2,5-Dimethyl | -Phenol |
| 3,4-Dimethyl | -Phenol |
| 2,6-Dimethyl | -Phenol |
| 4-n Propyl | -Phenol |
| 4-n-Butyl | -Phenol |
| 4-n-Amyl | -Phenol |
| 4-tert-Amyl | -Phenol |
| 4-n-Hexyl | -Phenol |
| 4-n-Heptyl | -Phenol |
| 2-Methoxy-4-(2-Propenyl)-Phenol (Eugenol) | |
| 2-Isopropyl-5-Methyl - Phenol (Thymol) | |
| Mono- and Poly-Alkyl and Aralkyl Halophenols | |
| Methyl | -p-Chlorophenol |
| Ethyl | -p-Chlorphenol |
| n-Propyl | -p-Chlorophenol |
| n-Butyl | -p-Chlorophenol |
| n-Amyl | -p-Chlorophenol |
| sec-Amyl | -p-Chlorophenol |
| n-Hexyl | -p-Chlorophenol |
| Cyclohexyl | -p-Chlorophenol |
| n-Heptyl | -p-Chlorophenol |
| n-Octyl | -p-Chlorophenol |
| O-Chlorophenol | |
| Methyl | -o-Chlorophenol |
| Ethyl | -o-Chlorophenol |
| n-Propyl | -o-Chlorophenol |
| n-Butyl | -o-Chlorophenol |
| n-Amyl | -o-Chlorophenol |
| tert-Amyl | -o-Chlorophenol |
| n-Hexyl | -o-Chlorophenol |
| n-Heptyl | -o-Chlorophenol |
| p-Chlorophenol | |
| o-Benzyl | -p-Chlorophenol |
| o-Benzyl-m-methyl | -p-Chlorophenol |
| o-Benzyl-m, m-dimethyl | -p-Chlorophenol |
| o-Phenylethyl | -p-Chlorophenol |
| o-Phenylethyl-m-methyl | -p-Chlorophenol |
| 3-Methyl | -p-Chlorophenol |
| 3,5-Dimethyl | -p-Chlorophenol |
| 6-Ethyl-3-methyl | -p-Chlorophenol |
| 6-n-Propyl-3-methyl | -p-Chlorophenol |
| 6-iso-propyl-3-methyl | -p-Chlorophenol |
| 2-Ethyl-3,5-dimethyl | -p-Chlorophenol |
| 6-sec Butyl-3-methyl | -p-Chlorophenol |
| 2-iso-Propyl-3,5-dimethyl | -p-Chlorophenol |
| 6-Diethylmethyl-3-methyl | -p-Chlorophenol |
| 6-iso-Propyl-2-ethyl-3-methyl | -p-Chlorophenol |
| 2-sec Amyl-3,5-dimethyl | -p-Chlorophenol |
| 2-Diethylmethyl-3,5-dimethyl | -p-Chlorophenol |
| 6-sec Octyl-3-methyl | -p-Chlorophenol |
| p-Bromophenol | |
| Methyl | -p-Bromophenol |
| Ethyl | -p-Bromophenol |
| n-Propyl | -p-Bromophenol |
| n-Butyl | -p-Bromophenol |
| n-Amyl | -p-Bromophenol |
| sec-Amyl | -p-Bromophenol |
| n-Hexyl | -p-Bromophenol |
| cyclohexyl | -p-Bromophenol |
| o-Bromophenol | |
| tert-Amyl | -o-Bromophenol |
| n-Hexyl | -o-Bromophenol |
| n-Propyl-m,m-Dimethyl | -o-Bromophenol |
| 2-Phenyl Phenol | |
| 4-Chloro-2-methyl phenol | |
| 4-chloro-3-methyl phenol | |
| 4-chloro-3,5-dimethyl phenol | |
| 2,4-dichloro-3,5-dimethyl phenol | |
| 3,4,5,6-tetrabromo-2-methylphenol | |
| 5-methyl-2-pentylphenol | |
| 4-isopropyl-3-methylphenol | |
| 5-chloro-2-hydroxydiphenyl methane | |
| Resorcinol and Its Derivatives | |
| Resorcinol | |
| Methyl | -Resorcinol |
| Ethyl | -Resorcinol |
| n-Propyl | -Resorcinol |
| n-Butyl | -Resorcinol |
| n-Amyl | -Resorcinol |
| n-Hexyl | -Resorcinol |
| n-Heptyl | -Resorcinol |
| n-Octyl | -Resorcinol |
| n-Nonyl | -Resorcinol |
| Phenyl | -Resorcinol |
| Benzyl | -Resorcinol |
| Phenylethyl | -Resorcinol |
| Phenylpropyl | -Resorcinol |

| | -continued |
|---|---|
| p-Chlorobenzyl | -Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |
| | Bisphenolic Compounds |
| Bisphenol A | |
| 2,2'-methylene bis (4-chlorophenol) | |
| 2,2'-methylene bis (3,4,6-trichlorophenol) (hexachlorophene) | |
| 2,2'-methylene bis (4-chloro-6-bromophenol) | |
| bis (2-hydroxy-3,5-dichlorophenyl) sulfide | |
| bis (2-hydroxy-5-chlorobenzyl) sulfide | |

The noncationic antibacterial agent is present in the dentifrice in an effective antiplaque amount, typically about 0.01–5% by weight, preferably about 0.03–1% and most preferably about 0.3–0.5%. The antibacterial agent is substantially water-insoluble, meaning that its solubility is less than about 1% by weight in water at 25° C. and may be even less than about 0.1%.

The preferred halogenated diphenyl ether and most preferred noncationic antibacterial agent other is triclosan. Preferred oehter noncationic antibacterial agents farnesol, nerolidol, bisabolol, santalol, phenol, thymol, eugenol, hexyl resorcinol and 2,2'methylene bis (4-chloro-6-bromophenol).

Triclosan is disclosed in aforementioned U.S. Pat. No. 4,022,880 as an antibacterial agent in combination with an anticalculur agent which provides zinc ions and in German Patent Disclosure 3532860 in combination with a copper compond. In European Patent Disclosure 0278744 it is disclosed in combination with a tooth desensitizing agent containing a source of potassium ions. It is also discosed as an antiplaque agent in a dentifrice formulated to contain a lamellar liquid crystal surfactant phase having a lamellar spacing of less than 6.0 nm and which may optionally contain a zinc salt in published European Patent Application 0161898 of Lane et al and in a dentifrice containing zinc citrate trihydrate in published European Patent Application 0161899 to Saxon et al.

Xylitol, which enhances the antiplaque effectiveness of the noncationic antibacterial agent may be employed in amounts ranging upward from about 0.1% by weight to about 40%. In amounts ranging upward from 0.1% by weight to about 5% or more it provides desirable sweetening to the dentifrice when present as the only sweetener or desirably mixed with another sweetener. It also provides desirable humectant character to the dentifrice and can be the sole humectant particularly when present in amounts of about 20–40%, although it is desirably mixed with another humectant. Preferably xylitol is present in amount of about 3–25% by weight, most preferably about 5–20%.

In the dentifrice, an orally acceptable vehicle including a water-phase with humectant is present. As stated, xylitol can be the sole humectant, although it is preferably mixed with another humectant, preferably glycerine and/or sorbitol. Water is present typically in amount of about 6% to 40% by weight, more typically about 15–35%, and humectant typically in amount of about 20–75% by weight of the dentifrice, more typically about 25–60%. Xylitol can be the sole humectant in amounts of about 20–40% by weight or can be mixed with additional humectant with humectant amounts of about 20–75% by weight total humectants. Reference hereto to sorbitol refers to the material typically as available commercially in 70% aqueous solutions.

The pH of such dentifrice of the invention is generally in the range of about 4.5 to about 9 or 10 and preferably about 6.5 to about 7.5. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In this invention, the dentifrice is substantially pasty in character, such as a tooth paste (dental cream). The dentifrice contains about 20–75% by weight of a dentally acceptable alkaline earth metal salt polishing material, examples of which polishing materials are tricalcium phosphate, dihydrated dicalcium phosphate, anhydrous dicalcium phosphate, calcium pyrophosphate, calcium carbonate, magnesium orthophosphate, trimagnesium phosphate, magnesium pyrophosphate and magnesium carbonate and mixtures thereof with each other. Mixtures containing about 20–75% by weight of the alkaline earth metal salt with other polishing agents such as insoluble sodium metaphosphate potassium metaphosphate, aluminum silicate, polishing materials such as zirconium silicate, material including the particulate thermosetting resins described in U.S. Pat. No. 3,070,510 issued Dec. 15, 1962, such as melamine-, phenolic, and ureaformaldehydes, and cross-linked polyepoxides and polyesters may also be used. The calcium polishing materials are preferred, and especially dicalcium phosphate dihydrate and B-calcium pyrophosphate are most preferred.

Toothpastes or dental cream typically contain a natural or synthetic thickener or gelling agent in proportions of about 0.1 to about 10%, preferably about 0.5 to about 5%. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$), and some water and trace metals. Its true specific gravity is 2.53 and it has an apparent bulk density (g./ml. at 8% moisture) of 1.0.

Other suitable thickeners or gelling agents or thickeners include Irish moss, iota-carrageenan, gum tragacanth, starch, polyvinylpyrrolidone, hydroxyethpropyl-cellulose, hydroxybutyl methyl cellulose, hydroxypropyl methyl cellulose, hydroxyethyl cellulose (e.g. available as Natrosol) and sodium carboxymethyl cellulose.

The dentifrice has anticaries effectiveness even without a fluoride ion source. However, it may also contain an anticaries amount of a fluoride ion source sufficient to supply about 25 ppm to 5000 ppm of fluoride ions to improve anticaries effectiveness.

The sources of fluoride ions, or fluorine-providing component are well known in the art as anti-caries agents. These compounds may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, or example sodium fluoride, potassium fluoride, ammonium fluoride, a copper fluoride such as cuprous fluoride, zinc fluoride, sodium flourosilicate, ammonium fluorosilicate, sodium fluorozirconate, sodium fluorozirconate, sodium monofluorophosphate, aluminum mono-and di-fluorophosphate and fluorinated sodium calcium pyrophosphate. Alkali metal and tin fluorides, such as sodium and stannous fluorides, sodium monofluorophosphate (MFP) and mixtures thereof, are preferred.

The amount of fluoride-providing compound, when present, is dependent to some extent upon the type of compound, its solubility, and the type of oral preparation, but it must be a non-toxic amount, generally about 0.0005 to about 3.0% in the preparation. In a dentifrice preparation, an amount of such compound which releases up to about 25 ppm about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion.

Typically, in the cases of alkali metal fluorides, this component is present in an amount up to about 2% by weight, based on the weight of the preparation, and preferably in the range of about 0.05% to 1%. In the case of sodium monofluorophosphate, the compound may be the present in an amount of about 0.1–3%, more typically about 0.76%.

It will be understood that, as is conventional, the oral preparations are to be sold or otherwise distributed in suitable labelled packages. Thus a toothpaste or cream will usually be in a collapsible tube typically aluminum, lined lead or plastic, or other squeeze, pump or pressurized dispenser for metering out the contents, having a label describing it, in substance, as a toothpaste, dental cream or the like.

In the present invention the antiplaque effectiveness of the noncationic antibacterial agent is substantially enhanced in the presence of xylitol and water-insoluble alkaline earth metal salt polishing agent, even when a special antibacterial-enhancing agent (AEA) is not present. However, such AEA may be present and its effect is particularly noted when the solubility of the calcium salt polishing agent is very low as is the case, for instance, with B-calcium pyrophosphate.

The antibacterial-enhancing agent which can enhance delivery of the noncationic antibacterial agent to, and retention thereof on, oral surfaces, when present, is employed in amounts effective to achieve such enhancement within the range in the oral composition of about 0.05 to about 4%, preferably about 0.1% to about 3%, more preferably about 0.5% to about 2.5% by weight.

The AEA may be a simple compound, preferably a polymerizable monomer, more preferably a polymer, which latter term is entirely generic, including for example oligomers, homopolymers, copolymers of two or more monomers, and the like. The AEA may be natural or synthetic, and water insoluble or preferably water (saliva) soluble or swellable (hydratable, hydrogel forming). It has an (weight) average molecular weight of about 100 to about 1,000,000, preferably about 1,000 to about 1,000,000, more preferably about 2,000 or 2,500 to about 250,000 or 500,000. The description of AEA's in ancestor U.S. Pat. No. 5,192,531 is incorporated herein by reference.

The AEA contains at least one delivery-enhancing group, and at least one organic retention-enhancing group.

As employed herein, the delivery-enhancing group refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces.

Preferably, the AEA is an anionic polymer and especially a polycarboxylate of molecular weight or about 1,000 to about 1,000,000 comprising a chain or backbone containing repeating units each preferably containing at least one carbon atom and preferably at least one directly or indirectly pendent, monovalent delivery-enhancing group and at least one directly or indirectly pendent monovalent retention-enhancing group geminally, vicinally or less preferably otherwise bonded to atoms, preferably carbon, in the chain. Preferred polycarboxylates are often employed in the form of their free acids or preferably partially or more preferably fully neutralized water soluble or water-swellable (hydratable, gel-forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (maleic anhydride) having a molecular weight (M.W.) of about 30,000 to about 1,000,000, most preferably about 30,000 to about 500,000. These copolymers are available for example as Gantrez, e.g. AM 139 (M.W. 5,000,000); AM 119 (M.W. 250,000); and preferably S-97 pharmaceutical grade (M.W. 70,000), of GAF Corporation.

Organic surface-active agents are used in the; compositions of the present invention to achieve increased prophylactic action. Moreover, they assist in achieving thorough and complete dispersion of the antiplaque agent throughout the oral cavity, and render the instant compositions more cosmetically acceptable. Indeed, at least one of surface-active agent or flavoring oil is present to effect desired solubilization of the antibacterial agent. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, higher fatty and esters of taurine and the substantially saturated higher aliphatic acyl amides of lower aliphatic amino carboxylic acid compounds, such as those having 12 to 16 carbons in the fatty acid, alkyl or acyl radicals, and the like. Examples of the last mentioned taurines and amides are N-methyl-N-cocoyl taurate, N-methyl-N-oleyl taurate, N-methyl-N-palmitoyl-taurate, N-lauroyl earcosine, and the sodium, potassium, and ethanolamine salts of N-lauroyl, N-myristoyl, or N-palmitoyl earcosine which should be substantially free from soap or similar higher fatty acid material. The use of these sarcosinate compounds in the oral compositions of the present invention is particularly advantageous since these materials exhibit a prolonged a marked effect in the inhibition of acid formation in the oral cavity due to carbohydrates breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.5–5% by weight, preferably about 1–2.5%. As indicated, surface active agent is believed to assist in the dissolving of the noncationic antibacterial agents.

Various other materials may be incorporated in the oral preparations of this invention such as whitening agents, preservatives, silicones, chlorophyll compounds and/or ammoniated material such as urea, diamonium phosphate, and mixtures thereof. These adjuvants, where present, are incorporated in the preparations in amounts which do not substantially adversely affect the properties and characteristics desired. Significant amounts of zinc, or other metal salts and materials, generally soluble, such as soluble alkaline earth metal salts, which would complex with active components of the instant invention may be less desirable to include.

Any suitable flavoring or sweetening material in addition to xylitol may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents for mixture with xylitol include sucrose, lactose, maltose, sorbitol, sodium cyclamate, perillartine, APM (aspartyl phenyl alanine, methyl ester), saccharine and the like, with (sodium) saccharine being preferred. Suitably, flavor and sweetening agents (excluding xylitol) each or together comprise from about 0.1% to 5% or more of the preparation. Moreover, flavor oil is believed to aid the dissolving of the antibacterial agent together with or even in the absence of surface-active agent.

In the preferred practice of this invention an oral composition containing the composition of the present invention is preferably applied regularly to dental enamel, such as every day or every second or third day or preferably from 1 to 3 times daily, at a pH of about 4.5 to about 9 or 10, generally about 5.5 to about 8, preferably about 6 to 8, for at least 2 weeks up to 8 weeks or more up to lifetime.

The following examples are further illustrative of the nature of the present invention, but it is understood that the invention is not limited thereto. All amounts and proportions referred to herein and in the appended claims are by weight, unless otherwise indicated.

EXAMPLE 1

A panel of twenty-five adults are given one of the test products below twice a day for seven days and the plaque of each was tested one week after the start of the test. The panelists do not eat or drink and refrain from oral hygiene on the morning of the test, when a plaque sample consisting of one half of their supragingival plaque is collected by a dental hygienist. The subjects then rinse with the test toothpaste slurries (1 part dentifrice, 2 parts water) for 30 seconds, expectorate, and then rinse with 5 ml of water for two seconds. Ten minutes after treatment as much as possible of the remaining plaque is collected. Plaque weights are then measured and used an indicator of how effective each dentifrice is as an anti-plaque composition. The procedure is then repeated with each of the other test toothpastes. The results shown below indicate that toothpaste containing insoluble calcium salt (dicalcium phosphate dihydrate) in combination with triclosan and xylitol is 15% more effective in reducing plaque when compared to the other test toothpastes (significant at the 95% level of confidence).

| Ingredients | Phosphate Dicalcium-Fluoride A | Placebo Dicalcium-Phosphate B | Dicalcium Phosphate Fluoride w/Xylitol C | Dicalcium Phosphate/Fluoride w/Xylitol and Triclosan D |
|---|---|---|---|---|
| Sodium Monofluoro phosphate | 0.76 | — | 0.76 | 0.76 |
| Triclosan | — | — | — | 0.30 |
| Dicalcium Phosphate Dihydrate | 48.76 | 48.76 | 40.00 | 40.00 |
| Deionized Water | 24.44 | 24.60 | 17.16 | 17.00 |
| Glycerin | 22.00 | 22.60 | 18.04 | 17.74 |
| Xylitol | — | — | 20.00 | 20.00 |
| Sodium Lauryl Sulfate | 1.20 | 1.20 | 1.20 | 1.50 |
| Flavor | 0.89 | 0.89 | 0.89 | 1.00 |
| Sodium Carboxymethyl-cellulose 7MF | 1.00 | 1.00 | — | — |
| Sodium Carboxymethyl-cellulose 12M31P | — | — | 0.70 | 0.70 |
| Iota-Carrageenan | — | — | 0.30 | 0.30 |
| Sodium Benzoate | 0.50 | 0.50 | 0.50 | — |
| Propylene glycol | — | — | — | 0.50 |
| Sodium Pyrophosphate | 0.25 | 0.25 | 0.25 | — |
| Sodium Saccharin | 0.20 | 0.20 | 0.20 | 0.20 |
| Total | 100.00 | 100.00 | 100.00 | 100.00 |

The average plaque weights collected from the panelists using each test toothpaste are as follows:

| Toothpaste | Plaque Weight - Milligrams |
|---|---|
| A | 10 |
| B | 10.4 |
| C | 10.3 |
| D | 8.8 |

The following dentifrices of Examples 2 to 7 are prepared:

EXAMPLE 2

|  | Percent |
| --- | --- |
| Sodium Monofluorophosphate | 0.76 |
| Triclosan | 0.30 |
| Dicalcium Phosphate Dihydrate | 48.76 |
| Deionized Water | 16.48 |
| Glycerin | 25.00 |
| Xylitol | 5.00 |
| Sodium Lauryl Sulfate | 1.20 |
| Flavor | 1.00 |
| Sodium Carboxymethyl Cellulose | 1.20 |
| Sodium Saccharin | 0.30 |

EXAMPLE 3

|  | Percent |
| --- | --- |
| Sodium Monofluorophosphate | 0.76 |
| Triclosan | 0.30 |
| Dicalcium Phosphate Dihyrate | 30.00 |
| Deionized Water | 25.44 |
| Xylitol | 40.00 |
| Sodium Lauryl Sulfate | 1.20 |
| Flavor | 1.00 |
| Sodium Carboxymethyl Cellulose | 1.00 |
| Sodium Saccharin | 0.30 |

EXAMPLE 4

|  | Percent |
| --- | --- |
| Sodium Monofluorophosphate | 0.76 |
| Triclosan | 0.30 |
| Calcium Carbonate | 40.00 |
| Deionized Water | 20.34 |
| Glycerin | 25.00 |
| Xylitol | 10.00 |
| Sodium Lauryl Sulfate | 1.20 |
| Flavor | 1.00 |
| Sodium Carboxymethyl Cellulose | 1.10 |
| Sodium Saccharin | 0.30 |

EXAMPLE 5

|  | Percent |
| --- | --- |
| Sodium Monofluorophosphate | 0.76 |
| Triclosan | 0.30 |
| β-Calcium Pyrophosphate | 40.00 |
| Gantrez S-97 Solution (13.5%) | 15.00 |
| Deionized Water | 10.44 |
| Glycerin | 25.00 |
| Xylitol | 5.00 |
| Sodium Lauryl Sulfate | 1.20 |
| Flavor | 1.00 |
| Sodium Carboxymethyl Cellulose | 1.00 |
| Sodium Saccharin | 0.30 |

EXAMPLE 6

|  | Percent |
| --- | --- |
| Sodium Monofluorophosphate | 0.76 |
| Triclosan | 0.30 |
| Dimagnesium Phosphate Heptahydrate | 40.00 |
| Gantrez S-97 Solution (13.5%) | 15.00 |
| Deionized Water | 22.44 |
| Glycerin | 15.00 |
| Xylitol | 3.00 |
| Sodium Lauryl Sulfate | 1.20 |
| Flavor | 1.00 |
| Sodium Carboxymethyl Cellulose | 1.00 |
| Sodium Saccharin | 0.30 |

EXAMPLE 7

|  | Percent |
| --- | --- |
| Sodium Monofluorophosphate | 0.00 |
| Triclosan | 0.30 |
| Dicalcium Phosphate Dihyrate | 5.00 |
| Calcium Carbonate | 35.00 |
| Deionized Water | 21.10 |
| Glycerin | 25.00 |
| Xylitol | 10.00 |
| Sodium Lauryl Sulfate | 1.20 |
| Flavor | 1.00 |
| Sodium Carboxymethyl Cellulose | 1.10 |
| Sodium Saccharin | 0.30 |

This invention has been described with respect to certain preferred embodiments and it will be understood that modifications and variations thereof obvious to those skilled in the art are to be included within the purview of this application and the scope of the appended claims.

We claim:

1. An antibacterial xylitol-enhanced fluoride dentifrice consisting essentially of in an orally acceptable aqueous humectant xylitol vehicle, about 20–75% by weight of a dentally acceptable water-insoluble calcium or magnesium alkaline earth metal polishing agent, non-toxic mount of a fluoride-providing compound in amount sufficient to release about 25 ppm to about 5,000 ppm of fluoride ion, an effective antiplaque amount of a substantially water-insoluble noncationic antibacterial antiplaque agent selected from the group consisting of halogenated diphenyl ethers, halogenated salicylanilides, benzoic esters, sesquiterpene alcohols, halogenated carbanilides and phenolic compounds and about 0.1 to about 40% by weight of xylitol, said dentifrice being free of pyrophosphate anticalculus agent in an effective anticalculus amount and of polycarboxylate or analogous antibacterial-enhancing agent in an amount which enhances the antiplaque effectiveness of said antibacterial antiplaque agent.

2. The dentifrice claimed in claim 1 wherein said antibacterial agent is present in amount of about 0.01–5% by weight.

3. The dentifrice claimed in claim 2 wherein said antibacterial agent is triclosan.

4. The dentifrice claimed in claim 3 wherein said amount of said antibacterial agent is about 0.3–0.5% by weight.

5. The dentifrice claimed in claim 1 wherein xylitol is present in amount of about 0.1–5% by weight.

6. The dentifrice claimed in claim 1 wherein xylitol is present is amount of about 3–25% by weight.

7. The dentifrice claimed in claim 6 wherein xylitol is present in amount of about 5–20% by weight.

8. The dentifrice claimed in claim 1 wherein xylitol is present in amount of about 20–40% by weight.

9. The dentifrice claimed in claim 1 wherein said alkaline earth metal polishing agent is a calcium salt.

10. The dentifrice claimed in claim 9 wherein said polishing agent is dihydrated dicalcium phosphate.

11. The dentifrice claimed in claim 9 wherein said calcium salt is β-calcium pyrophosphate.

12. The dentifrice in claim 9 wherein said calcium salt is calcium carbonate.

13. The dentifrice claimed in claim 1 wherein said dentifrice additionally comprises about 0.5–5% by weight of an organic surface-active agent.

14. The dentifrice claimed in claim 1 wherein said dentifrice additionally comprises about 0.1–5% by weight of a flavoring oil.

15. A method of inhbiting plaque formation comprising applying the dentifrice claimed in claim 1 to dental enamel.

* * * * *